(12) United States Patent
Fantasia et al.

(10) Patent No.: US 9,505,759 B2
(45) Date of Patent: Nov. 29, 2016

(54) PD-CATALYZED COUPLING OF PYRAZOLE AMIDES

(71) Applicant: Hoffmann-La Roche Inc., Little Falls, NJ (US)

(72) Inventors: Serena Maria Fantasia, Basel (CH); Kurt Puentener, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/925,544

(22) Filed: Oct. 28, 2015

(65) Prior Publication Data
US 2016/0046628 A1 Feb. 18, 2016

Related U.S. Application Data

(63) Continuation of application No. PCT/EP2014/058549, filed on Apr. 28, 2014.

(30) Foreign Application Priority Data

Apr. 30, 2013 (EP) .................................... 13166027

(51) Int. Cl.
*C07D 401/14* (2006.01)
*C07D 401/02* (2006.01)
*C07D 401/10* (2006.01)
*C07D 471/04* (2006.01)

(52) U.S. Cl.
CPC .................. *C07D 471/04* (2013.01)

(58) Field of Classification Search
CPC . C07D 401/02; C07D 401/10; C07D 401/14
USPC ................................. 546/119, 121
See application file for complete search history.

(56) References Cited

U.S. PATENT DOCUMENTS 8,017,604 B2 * 9/2011 Alberati ............... A61K 31/437
514/233.2

FOREIGN PATENT DOCUMENTS

| WO | 2011/036127 A1 | 3/2011 |
| WO | 2012/076430 A1 | 6/2012 |
| WO | 2013/041472 A1 | 3/2013 |

OTHER PUBLICATIONS

International Preliminary Report on Patentability for App. Ser. No. PCT/EP2014/058549, mailed Jun. 26, 2014, 3 pages.

* cited by examiner

Primary Examiner — Niloofar Rahmani

(57) ABSTRACT

A novel process for the preparation of imidazo[1,2-a]pyridine compounds of the formula

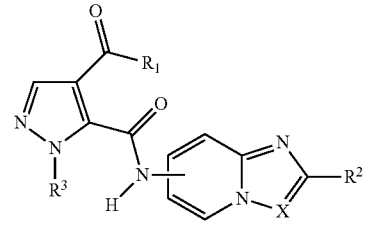

wherein
$R^1$ is $C_{1-4}$-alkoxy or $NR^4R^5$ wherein
$R^4$ and $R^5$ are independently hydrogen or $C_{1-4}$-alkyl or
$R^4$ and $R^5$, together with the nitrogen atom to which they are attached, form a saturated 4- to 6-membered heterocyclic ring which may contain one further heteroatom selected from nitrogen or oxygen;
$R^2$ is $C_{1-4}$-alkyl, $C_{1-4}$-alkoxycarbonyl, halogen, phenyl which is optionally substituted with $C_{1-4}$-alkyl, $C_{1-4}$-alkoxy or halogen or is $NR^4R^5$ wherein
$R^4$ and $R^5$ are independently hydrogen or $C_{1-4}$-alkyl or
$R^4$ and $R^5$, together with the nitrogen atom to which they are attached, form a saturated 4- to 6-membered heterocyclic ring which may contain one further heteroatom selected from nitrogen or oxygen;
$R^3$ is $C_{1-4}$-alkyl and
X is nitrogen or CH
is described.
The imidazo[1,2-a]pyridine compounds of the formula I are either precursors for active principles or active principles itself, acting as phosphodiesterase (PDE) inhibitors, particularly PDE10 inhibitors which have the potential to treat psychotic disorders like schizophrenia (Int. Patent Publication WO 2012/076430).

11 Claims, No Drawings

PD-CATALYZED COUPLING OF PYRAZOLE AMIDES

CROSS REFERENCE TO RELATED APPLICATIONS

This application is a continuation of International Application No. PCT/EP2014/058549 having an international filing date of Apr. 28, 2014, the entire contents of which are incorporated herein by reference, and which claims benefit under 35 U.S.C. §119 to European Patent Application No. 13166027.6 filed Apr. 30, 2013.

The present invention relates to a novel process for the preparation of imidazo[1,2-a]pyridine compounds of the formula

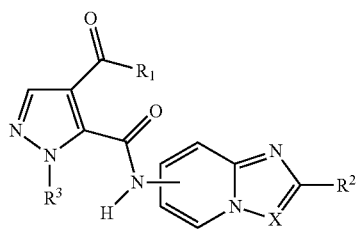

I wherein
$R^1$ is $C_{1-4}$-alkoxy or $NR^4R^5$ wherein
  $R^4$ and $R^5$ are independently hydrogen or $C_{1-4}$-alkyl or
  $R^4$ and $R^5$, together with the nitrogen atom to which they are attached, form a saturated 4- to 6-membered heterocyclic ring which may contain one further heteroatom selected from nitrogen or oxygen;
$R^2$ is $C_{1-4}$-alkyl, $C_{1-4}$-alkoxycarbonyl, halogen, phenyl which is optionally substituted with $C_{1-4}$-alkyl, $C_{1-4}$-alkoxy or halogen or is $NR^4R^5$ wherein
  $R^4$ and $R^5$ are independently hydrogen or $C_{1-4}$-alkyl or
  $R^4$ and $R^5$, together with the nitrogen atom to which they are attached, form a saturated 4- to 6-membered heterocyclic ring which may contain one further heteroatom selected from nitrogen or oxygen;
$R^3$ is $C_{1-4}$-alkyl and
X is nitrogen or CH.

The imidazo[1,2-a]pyridine compounds of the formula I are either precursors for active principles or active principles itself, acting as phosphodiesterase (PDE) inhibitors, particularly PDE10 inhibitors. PDE10 inhibitors have the potential to treat psychotic disorders like schizophrenia (Int. Patent Publication WO 2012/076430).

According to the Int. Patent Publication WO 2012/076430 (see particularly scheme 1, page 26) commonly known amide formation methods can be applied for the formation of the desired compounds. For instance a pyrazine carboxylic acid derivative can be activated with a coupling agent prior to the reaction with the imidazo[1,2-a]pyridine moiety or in another embodiment the acid chloride of the pyrazine carboxylic acid is reacted with the imidazo[1,2-a]pyridine moiety.

Object of the present invention therefore was to find a more effective synthetic approach which is scalable and which affords the desired imidazo[1,2-a]pyridine compounds of the formula I with high selectivity and high yield.

This object could be achieved with the process of the present invention as described below.

The process for the preparation of the imidazo[1,2-a]pyridine compounds of the formula

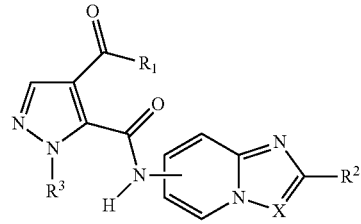

I wherein
$R^1$ is $C_{1-4}$-alkoxy or $NR^4R^5$ wherein
  $R^4$ and $R^5$ are independently hydrogen or $C_{1-4}$-alkyl or
  $R^4$ and $R^5$, together with the nitrogen atom to which they are attached, form a saturated 4- to 6-membered heterocyclic ring which may contain one further heteroatom selected from nitrogen or oxygen;
$R^2$ is $C_{1-4}$-alkyl, $C_{1-4}$-alkoxycarbonyl, halogen, phenyl which is optionally substituted with $C_{1-4}$-alkyl, $C_{1-4}$-alkoxy or halogen or is $NR^4R^5$ wherein
  $R^4$ and $R^5$ are independently hydrogen or $C_{1-4}$-alkyl or
  $R^4$ and $R^5$, together with the nitrogen atom to which they are attached, form a saturated 4- to 6-membered heterocyclic ring which may contain one further heteroatom selected from nitrogen or oxygen;
$R^3$ is $C_{1-4}$-alkyl and
X is nitrogen or CH;
comprises the reaction of a pyrazole carboxamide derivative of formula

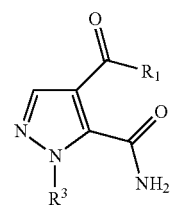

II wherein $R^1$ and $R^3$ are as above;
with a imidazo[1,2-a]pyridine derivative of the formula

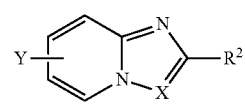

III wherein $R^2$ and X are as above and
Y stands for halogen, $C_{1-4}$-alkylsulfonyloxy, mono- or polyhalogen-$C_{1-4}$-alkylsulfonyloxy, mono- or poly-$C_{1-4}$-alkylphenylsulfonyloxy or phenylsulfonyloxy;
in the presence of a palladium catalyst, a base and an organic solvent.

Unless otherwise indicated the following definitions are set forth to illustrate and define the meaning and scope of the various terms used to describe the invention herein.

The term "$C_{1-4}$-alkyl" alone or combined with other groups, refers to a branched or straight chained monovalent saturated aliphatic hydrocarbon radical of one to four carbon atoms. This term can be exemplified by radicals like methyl, ethyl, n-propyl, i-propyl, n-butyl, s-butyl or t-butyl. Particularly the term $C_{1-4}$-alkyl refers to methyl or ethyl.

The term "$C_{1-4}$-alkoxy" stands for a $C_{1-4}$-alkyl group as defined above which is attached to an oxygen radical. This term can be exemplified by radicals like methoxy, ethoxy, n-propoxy, i-propoxy, n-butoxy, i-butoxy or t-butoxy. Particularly the term $C_{1-4}$-alkoxy refers to methoxy or ethoxy.

The term "$C_{1-4}$-alkoxycarbonyl" stands for a $C_{1-4}$-alkoxy group as defined above which is attached to carbonyl radical. This term can be exemplified by radicals like methoxy carbonyl, ethoxy carbonyl, n-propoxy carbonyl i-propoxy carbonyl, n-butoxy carbonyl, i-butoxy carbonyl or t-butoxy carbonyl. Particularly the term $C_{1-4}$-alkoxy carbonyl refers to methoxy carbonyl or ethoxy carbonyl.

The term "$C_{1-4}$-alkylsulfonyloxy" stands for a $C_{1-4}$-alkyl group as defined above which is attached to a sulfonyloxy radical. The term can be exemplified by a radical like methylsulfonyloxy (mesyloxy).

The term "mono- or polyhalogen-$C_{1-4}$-alkylsulfonyloxy" stands for a "$C_{1-4}$-alkylsulfonyloxy" group as defined above, wherein one or multiple hydrogen atoms of the alkyl chain are replaced by a halogen atom. The term can be exemplified by a radical like nonafluorbutanesulfonyloxy (nonaflate).

The term "mono- or poly-$C_{1-4}$-alkylphenylsulfonyloxy" stands for a phenylsulfonyloxy group which is mono- or polysubstituted with $C_{1-4}$-alkyl radicals. The term can be exemplified by a radical like p-toluenesulfonyloxy.

The term "mono- or polyhalogen-$C_{1-4}$-alkyl" stands for $C_{1-4}$-alkyl as defined above which is mono- or polysubstituted with a halogen atom. An example for this term is trifluoromethyl.

The term "saturated 4- to 6-membered heterocyclic ring" refers to the substituent $R^4$ and $R^5$ which, together with the nitrogen atom to which they are attached form said saturated 4- to 6-membered heterocyclic ring which may in addition contain one further heteroatom selected from nitrogen or oxygen. Examples of such rings are azetidine, piperidine, piperazine or 4-morpholine.

The term halogen refers to fluorine, chlorine, bromine or iodine.

The pyrazole carboxamide derivatives of formula II are either commercially available or can be prepared according to methods known to the skilled in the art from the respective pyrazole carboxylic acid derivative for instance by activating the pyrazole carboxylic acid derivative with 1,1'-carbonyldiimidazole and by subsequent amidation with ammonia. The pyrazole carboxylic acid derivatives can for instance be prepared following methods described in the Int. Patent Publication WO 2012/076430 (scheme 3, page 27).

The halogen imidazo[1,2-a]pyridine derivatives of the formula III are either commercially available or can be prepared according to methods known in the art, for example as described in Ueda et al. *J. Am. Chem. Soc.* 2009, 131, 15080-15081 or in the Int. Patent Publication WO 2012/076430 (Scheme 6, page 29).

In a particular embodiment of the present invention the halogen imidazo[1,2-a]pyridine derivative has the formula IIIb wherein $R^2$, X and Y are as above.

Particularly Y stands for chlorine, bromine, iodine, nonafluorbutanesulfonyloxy, mesityloxy or p-toluenesulfonyloxy.

More particularly Y stands for bromine or iodine and X and $R^2$ are as above.

The reaction of the pyrazole carboxamide derivatives of formula II with the halogen imidazo[1,2-a]pyridine derivative of the formula III is characterized by the presence of a palladium catalyst, a base and an organic solvent.

The palladium catalyst comprises a palladium source and a ligand of the formula

IV wherein
$R^6$ is hydrogen or $C_{1-4}$-alkyl;
$R^7$ and $R^8$ are independently of each other $C_{1-4}$-alkyl;
$R^9$ and $R^{10}$ are independently of each other $C_{1-4}$-alkyl, $C_{3-7}$-cycloalkyl, di-($C_{1-4}$-alkyl)-amino or phenyl which is optionally substituted with $C_{1-4}$-alkyl or $C_{1-4}$-alkoxy or
$R^9$ and $R^{10}$ together form a cycle of the formula The ligand particularly is Xantophos, a compound of formula IV wherein
$R^6$ is hydrogen;
$R^7$ and $R^8$ are methyl;
$R^9$ and $R^{10}$ are phenyl.

The palladium source can be selected from Bis(dibenzylideneacetone)palladium(0), [Pd(dba)$_2$]; Tris(dibenzylideneacetone)dipalladium(0), [Pd$_2$(dba)$_3$]; Tris(dibenzylideneacetone)dipalladium(0)-chloroform adduct), [Pd$_2$(dba)$_3$·CHCl$_3$]; Palladium(II) acetate, [Pd(OAc)$_2$]; Palladium(II) acetylacetonate, [Pd(acac)$_2$]; Bis(acetonitrile dichloropalladium(II)), [PdCl$_2$(CH$_3$CN)$_2$]; Palladium(II)Trifluoroacetate, [Pd(O$_2$CCF$_3$)$_2$]; di-µ-chlorobis[2-[(dimethylamino)methyl]phenyl-C,N]dipalladium(II), [Pd(C,N-Me$_2$NCH$_2$Ph)Cl$_2$]; Allylpalladium(II) chloride dimer, [Pd(allyl)Cl$_2$], but particularly from Tris(dibenzylideneacetone)dipalladium(0)), [Pd$_2$(dba)$_3$] or from the Tris(dibenzylideneacetone)dipalladium(0)-chloroform adduct, [Pd$_2$(dba)$_3$·CHCl$_3$].

As a rule the Pd catalyst is generated in situ by suspending the palladium source with the ligand in a polar aprotic solvent, such as in ethers like methyl tert-butyl ether, cyclopentyl methyl ether, dioxane or tetrahydrofuran or in halogenated hydrocarbons such as in dichloromethane, but particularly in tetrahydrofuran.

The base usually is either an organic base which can be selected from trialkylamines such as triethyl amine or di-isopropyl ethyl amine, from amidines such as 1,8-diazabicyclo[5.4.0]undec-7-en from alkali alcoholates such as sodium-, or potassium ethylate or sodium- or potassium t-butylate and from alkali acetates such as sodium acetate or is an inorganic base which can be selected from alkali- or alkali earth carbonates or hydrogencarbonates such as lithium-, sodium-, potassium- or cesium carbonate or hydrogencarbonate, from alkali hydroxides such as sodium hydroxide or from alkali phosphates or -hydrogen phosphates such as sodium- or potassium phosphate or hydrogen phosphate.

Particular good results have been obtained with potassium carbonate.

The organic solvent present ideally is a polar protic solvent or a mixture of a polar protic solvent and a polar aprotic solvent.

Suitable polar protic solvents are lower aliphatic alcohols such as ethanol or t-butanol, but particularly ethanol.

Suitable polar aprotic solvents are ethers like methyl tert-butyl ether, cyclopentyl methyl ether, dioxane or tetrahydrofuran or in halogenated hydrocarbons such as in dichloromethane, but particularly in tetrahydrofuran. More particularly the organic solvent is ethanol or a mixture of ethanol and tetrahydrofuran The reaction is usually performed at a reaction temperature of 20° C. to 150° C., particularly at 70° C. to 110° C.

In a particular embodiment of the present invention the imidazo[1,2-a]pyridine has the formula

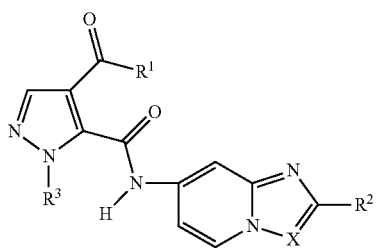

Ib wherein $R^1$, $R^2$ and $R^3$ are as above.
More particularly
$R^1$ is $C_{1-4}$-alkoxy or $NR^4R^5$ wherein
$R^4$ and $R^5$ are independently $C_{1-4}$-alkyl or
$R^4$ and $R^5$, together with the nitrogen atom to which they are attached, form a saturated 4- to 6-membered heterocyclic ring which may contain one further heteroatom selected from oxygen;
$R^2$ is $C_{1-4}$-alkoxycarbonyl, halogen, phenyl which is optionally substituted with halogen or is $NR^4R^5$ wherein
$R^4$ and $R^5$, together with the nitrogen atom to which they are attached, form a saturated 4- to 6-membered heterocyclic ring which may contain one further heteroatom selected from oxygen;
$R^3$ is $C_{1-4}$-alkyl and
X is nitrogen or CH.
Even more particularly
$R^1$ is ethoxy or $NR^4R^5$ wherein
$R^4$ and $R^5$ are ethyl or $R^4$ and $R^5$, together with the nitrogen atom to which they are attached, form a azetidine or a 4-morpholine ring;
$R^2$ is ethoxycarbonyl, halogen, phenyl which is optionally substituted with halogen or is $NR^4R^5$ wherein
$R^4$ and $R^5$, together with the nitrogen atom to which they are attached, form a 4-morpholine ring;
$R^3$ is methyl and
X is nitrogen or CH.

Upon completion of the reaction the desired product can be isolated following methods well known to the skilled in the art, for instance the solvent can be distilled off and the residue can be further purified by crystallization in a suitable organic solvent.

EXAMPLES

Abbreviations

Xantphos=4,5-bis-(diphenylphosphino)-9,9-dimethylxanthene; t-BuOH=tertiary butanol; EtOH=ethanol; THF=tetrahydrofuran; Me-THF=2-methyl tetrahydrofurane; HRMS=high resolution mass spectroscopy; $Pd_2(dba)_3$·$CHCl_3$=tris(dibenzylideneacetone)di-palladium(0) chloroform adduct; $[Pd(allyl)Cl]_2$=allylpalladium(II) chloride dimer; $Pd(OAc)_2$=palladium(II) acetate; $Pd(acac)_2$=palladium(II) acetylacetonate; $Pd(CH_3CN)_2Cl_2$=bis(acetonitrile)dichloropalladium(II); $[Pd(C,N-Me_2NCH_2Ph)Cl]_2$=di-µ-chlorobis[2-[(dimethylamino)methyl]phenyl-C,N] dipalladium(II); $Pd(O_2CCF_3)_2$=palladium(II) trifluoroacetate; T3P=1-propanephosphonic acid anhydride cyclic trimer; TLC=thin layer chromatography; DCM=dichloromethane.

Example A

Ethyl 5-carbamoyl-1-methyl-1H-pyrazole-4-carboxylate

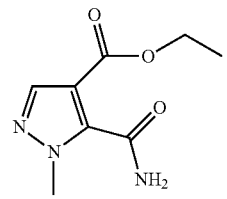

To a solution of 4-(ethoxycarbonyl)-1-methyl-1H-pyrazole-5-carboxylic acid (100.0 g, 0.50 mol) in THF (1 L), 1,1'-carbonyldiimidazole (92.0 g, 0.55 mol) was added and the resulting yellowish solution was stirred for 2 h at r.t. After, the reaction mixture was cooled to 10° C. gaseous ammonia was bubbled through the reaction mixture for approx. 30 min. To the formed suspension, water (1 L) was added and the resulting yellowish solution was concentrated at 40° C./100 mbar to a volume of approx. 1 L. The formed white suspension was cooled over night at 5° C. and filtered afterwards. The filter cake was washed with ice-cold water (200 mL) and heptane (500 mL) and dried at 40° C./100 mbar to afford 91.2 g of ethyl 5-carbamoyl-1-methyl-1H-pyrazole-4-carboxylate (92% yield) as white crystals.

MS: m/z=198.10 (M+H)$^+$.

Example B

5-Carbamoyl-1-methyl-1H-pyrazole-4-carboxylic acid sodium salt

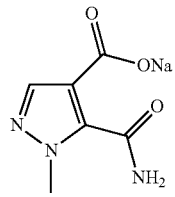

A solution of ethyl 5-carbamoyl-1-methyl-1H-pyrazole-4-carboxylate (26.0 g, 131 mmol) in THF (600 mL) and 2N aqueous sodium hydroxide (78 mL, 157 mmol) was stirred at r.t. for 28 h. The formed suspension was filtered, the filter cake washed with THF (100 mL) and dried 40° C./100 mbar to yield 24.8 g of 5-carbamoyl-1-methyl-1H-pyrazole-4-carboxylic acid sodium salt (>99% yield) as a white solid.

MS: m/z=168.0 (M−Na)⁻

Example C 4-(azetidine-1-carbonyl)-1-methyl-1H-pyrazole-5-carboxamide

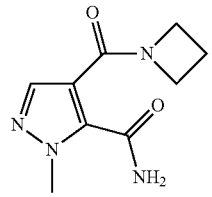

To a suspension of 5-carbamoyl-1-methyl-1H-pyrazole-4-carboxylic acid sodium salt (20.0 g, 105 mmol) in ethyl acetate (200 mL), a solution of T3P in ethyl acetate (260 mL, 445 mmol) was added at r.t. The reaction mixture was heated to 50° C. Then, azetidine (24.4 g, 419 mmol) was added within 30 min and after 40 min at 50° C. the formed yellowish solution was allowed to cool to r.t. The reaction mixture was evaporated to dryness (40° C./100 mbar). The residue was dissolved in dichloromethane (400 mL) and the formed organic solution was washed with water (200 mL), dried over sodium sulfate and evaporated to dryness (40° C./100 mbar) to afford 15.5 g of crude product. Crystallization from heptane/ethyl acetate yielded 13.8 g of 4-(azetidine-1-carbonyl)-1-methyl-1H-pyrazole-5-carboxamide (63% yield) as white crystals.

MS: m/z=209.10 (M+H)⁺.

Example D 4-(Dimethylaminocarbonyl)-1-methyl-1H-pyrazole-5-carboxamide

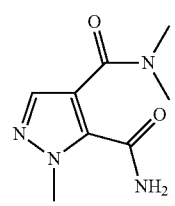

To a suspension of 5-carbamoyl-1-methyl-1H-pyrazole-4-carboxylic acid sodium salt (15.4 g, 79 mmol) in ethyl acetate (200 mL), a solution of T3P in ethyl acetate (207 mL, 355 mmol) was added at r.t. The reaction mixture was heated to 50° C., dimethylamine hydrochloride (25.8 g, 316 mmol) and diisopropylethylamine (61.2 g, 474 mmol) were added. After 2.5 h at 50° C., the reaction mixture was allowed to cool to r.t., water (200 mL) was added to the reaction mixture and the organic layer separated. The aqueous phase was washed 3 times with ethyl acetate (200 mL) and the combined organic phases were evaporated to dryness (40°/100 mbar) to yield 55 g of crude product as a yellowish oil. After silica gel chromatography and subsequent crystallization from heptane/ethyl acetate, 6.1 g of 4-(dimethylaminocarbonyl)-1-methyl-1H-pyrazole-5-carboxamide (40% yield) were isolated as a white, crystalline solid.

MS: m/z=197.10 (M+H)⁺.

Example E

1-Methyl-4-(4-morpholinylcarbonyl)-1H-pyrazole-5-carboxamide

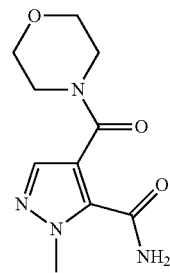 [SMILES: Cn1ncc(C(=O)N2CCOCC2)c1C(N)=O]

To a suspension of 1-methyl-4-(4-morpholinylcarbonyl)-1H-pyrazole-5-carboxylic acid (17.0 g, 71 mmol) in THF (200 mL), 1,1'-carbonyldiimidazole (14.3 g, 85 mmol) was added and the resulting yellowish solution was stirred for 2 h at r.t. After, the reaction mixture was cooled to 10° C. and gaseous ammonia was bubbled through the reaction mixture for approx. 30 min. The formed suspension was concentrated at 40° C./100 mbar to a total volume of approx. 50 mL, then dichloromethane (500 ml) was added and the formed organic solution was washed successively with aqueous solutions of citric acid (100 mL), ammonium chloride (50 mL) and sodium chloride (50 mL). The organic layer was dried over sodium sulfate and evaporated to dryness to afford 15.3 g of 1-methyl-4-(4-morpholinylcarbonyl)-1H-pyrazole-5-carboxamide (90% yield) as white crystalline solid.

MS: m/z=238.1 (M)⁺.

Example 1.1

1-Methyl-5-(2-phenyl-imidazo[1,2-a]pyridin-7-yl-carbamoyl)-1H-pyrazole-4-carboxylic acid ethyl ester

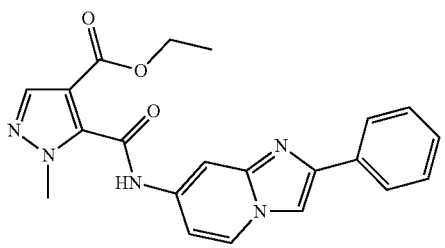 [SMILES: CCOC(=O)c1cnn(C)c1C(=O)Nc1ccn2cc(-c3ccccc3)nc2c1]

A suspension of tris(dibenzylideneacetone)dipalladium-chloroform adduct (2.3 mg, 2.3×10⁻³ mmol) and Xantphos (2.7 mg, 4.5×10⁻³ mmol) in THF (1 mL) was added under argon to a pressure vessel containing ethyl 5-carbamoyl-1-methyl-1H-pyrazole-4-carboxylate (188 mg, 942×10⁻³ mmol), 7-bromo-2-phenylimidazo[1,2-a]pyridine (250 mg, 906×10⁻³ mmol), potassium carbonate (152 mg, 1.1 mmol) and EtOH (4 mL). The reaction mixture was heated at 100° C. for three hours. The yellow suspension was then cooled to room temperature and the solvent was evaporated under reduced pressure. HPLC analysis of the residue showed >99% conversion (retention times: 2.39 min (ethyl 5-carbamoyl-1-methyl-1H-pyrazole-4-carboxylate), 4.45 min (7-bromo-2-phenylimidazo[1,2-a]pyridine), 4.57 min (1-methyl-5-(2-phenyl-imidazo[1,2-a]pyridin-7-ylcarbamoyl)-1H-pyrazole-4-carboxylic acid ethyl ester)). The crude product (83% HPLC purity) was suspended in t-BuOH (5 mL) and filtered. The solid was washed with water and EtOH and then dried under vacuum. 1-Methyl-5-(2-phenyl-imidazo[1,2-a]pyridin-7-ylcarbamoyl)-1H-pyrazole-4-carboxylic acid ethyl ester was obtained as a light green solid (319 mg, 90% yield) with 94% purity (HPLC area-%).

HRMS: m/z=390.17 (M+H)+.

Condition of the HPLC analysis: Agilent 1100 with UV detector, XBridge C18 Column, 2.5 m, 50×4.6 mm. Column Temperature: 40° C., flow rate: 1.5 mL/min, UV detection: 252 nm, mobile phase: A=water/acetonitrile 95:5, B=acetonitrile, C=7.71 g of ammonium acetate dissolved in 950 g of water and 40 g acetonitrile. The gradient applied is shown in table 1.

TABLE 1

| Time (min) | A (%) | B (%) | C (%) |
|---|---|---|---|
| 0 | 90 | 0 | 10 |
| 6 | 5 | 85 | 10 |
| 7 | 5 | 85 | 10 |

Examples 1.2 to 1.7

Example 1.1 was repeated with different palladium sources. Conversion and product yields were determined with the HPLC method disclosed in Example 1.1

TABLE 2

| Example | Pd Source | Conversion [%] | Yield [%] |
|---|---|---|---|
| 1.2 | [Pd(allyl)Cl]₂ | >99 | 73 |
| 1.3 | Pd(OAc)₂ | >99 | 70 |
| 1.4 | Pd(acac)₂ | >99 | 66 |
| 1.5 | Pd(CH₃CN)₂Cl₂ | >99 | 69 |
| 1.6 | [Pd(C,N—Me₂NCH₂Ph)Cl]₂ | >99 | 73 |
| 1.7 | Pd(O₂CCF₃)₂ | >99 | 76 |

Example 2

1-Methyl-5-(2-phenyl-imidazo[1,2-a]pyridin-7-yl-carbamoyl)-1H-pyrazole-4-carboxylic acid ethyl ester

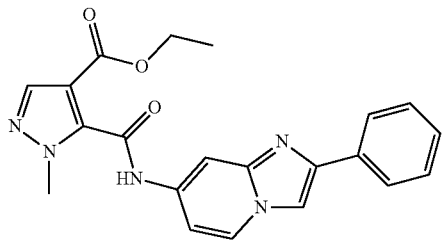 [SMILES: CCOC(=O)c1cnn(C)c1C(=O)Nc1ccn2cc(-c3ccccc3)nc2c1]

A suspension of tris(dibenzylideneacetone)dipalladium-chloroform adduct (46.9 mg, 45.3×10⁻³ mmol) and xantphos (53.5 mg, 90.7×10⁻³ mmol) in THF (20 mL) was added under argon to a pressure vessel containing ethyl 5-carbamoyl-1-methyl-1H-pyrazole-4-carboxylate (3.80 g, 19.1 mmol), 7-bromo-2-phenylimidazo[1,2-a]pyridine (5.00 g, 18.3 mmol), potassium carbonate (3.10 g, 21.8 mmol) and EtOH (80 mL). The reaction mixture was heated at 100° C. for three hours. The yellow suspension was then cooled to room temperature and the solvent was evaporated under reduced pressure. HPLC analysis of the residue showed >99% conversion (HPLC method cf. example 1.1. Retention times: 2.39 min (ethyl 5-carbamoyl-1-methyl-1H-pyrazole-4-carboxylate), 4.45 min (7-bromo-2-phenylimidazo[1,2-a]pyridine), 4.57 min (1-methyl-5-(2-phenyl-imidazo[1,2-a]pyridin-7-ylcarbamoyl)-1H-pyrazole-4-carboxylic acid ethyl ester)). The residue was suspended in t-BuOH (150 mL) and filtered. The crude product (quantitative yield, 90% purity (HPLC area-%)) was washed with an aqueous solution of potassium carbonate (1 mol/L) and then with water. After drying under vacuum, 1-methyl-5-(2-phenyl-imidazo[1,2-a]pyridin-7-ylcarbamoyl)-1H-pyrazole-4-carboxylic acid ethyl ester was obtained as a light green solid (4.46 g, 63% yield) with 98% purity (HPLC area-%).

Example 3

4-(Azetidine-1-carbonyl)-2-methyl-2H-pyrazole-3-carboxylic acid (2-phenyl-imidazo[1,2-a]pyridin-7-yl)-amide

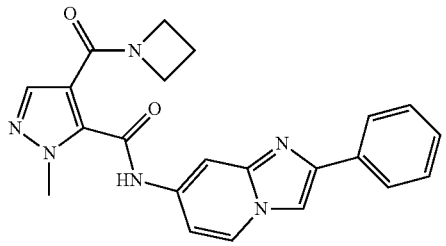 [SMILES: Cn1ncc(C(=O)N2CCC2)c1C(=O)Nc1ccn2cc(-c3ccccc3)nc2c1]

A suspension of tris(dibenzylideneacetone)dipalladium-chloroform adduct (94.7 mg, 91.5×10⁻³ mmol) and xantphos (108 mg, 183×10⁻³ mmol) in THF (20 mL) was added under argon to a 4-neck-round bottom flask containing 4-(azetidine-1-carbonyl)-1-methyl-1H-pyrazole-5-carboxamide (4.00 g, 19.2 mmol), 7-bromo-2-phenylimidazo[1,2-a]pyridine (5.00 g, 18.3 mmol), potassium carbonate (3.10 g, 21.8 mmol) and EtOH (80 mL). The reaction mixture was heated at 80° C. for five hours. HPLC analysis of the reaction mixture showed >99% conversion with 86% purity (HPLC method cf. example 1.1. Retention times: 1.51-1.70 min (4-(azetidine-1-carbonyl)-1-methyl-1H-pyrazole-5-carboxamide), 4.15 min (4-(azetidine-1-carbonyl)-2-methyl-2H-pyrazole-3-carboxylic acid (2-phenyl-imidazo[1,2-a]pyridin-7-yl)-amide), 4.45 min (7-bromo-2-phenylimidazo[1,2-a]pyridine)). The yellow suspension was then cooled to room temperature and the solvent was evaporated under reduced pressure. The residue was crystallized from Me-THF. 4-(Azetidine-1-carbonyl)-2-methyl-2H-pyrazole-3-carboxylic acid (2-phenyl-imidazo[1,2-a]pyridin-7-yl)-amide was obtained as a yellow crystalline solid (4.44 g, 61% yield) with 98% purity (HPLC area-%).

HRMS: m/z=401.17 (M+H)+.

Example 4

2-Methyl-2H-pyrazole-3,4-dicarboxylic acid 4-dimethylamide 3-[(2-phenyl-imidazo[1,2-a]pyridin-7-yl)-amide]

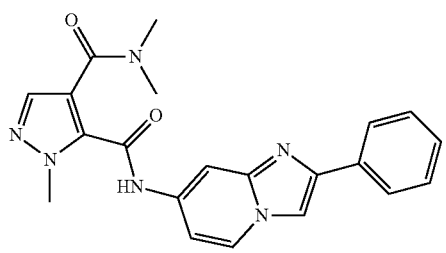 [SMILES: CN(C)C(=O)c1cnn(C)c1C(=O)Nc1ccn2cc(-c3ccccc3)nc2c1]

A suspension of tris(dibenzylideneacetone)dipalladium-chloroform adduct (9.5 mg, 9.2×10⁻³ mmol) and xantphos (10.8 mg, 18.3×10⁻³ mmol) in THF (2 mL) was added under argon to a 4-neck-round bottom flask containing 4-(Dimethylaminocarbonyl)-1-methyl-1H-pyrazole-5-carboxamide (377 mg, 1.9 mmol), 7-bromo-2-phenylimidazo[1,2-a]pyridine (500 mg, 1.8 mmol), potassium carbonate (307 mg, 2.2 mmol) and EtOH (8 mL). The reaction mixture was heated at 80° C. for three hours. HPLC analysis of the reaction mixture showed >99% conversion (92% purity) (HPLC method cf. example 1.1. Retention times: 1.08 min (4-(Dimethylaminocarbonyl)-1-methyl-1H-pyrazole-5-carboxamide), 3.96 min (2-methyl-2H-pyrazole-3,4-dicarboxylic acid 4-dimethylamide 3-[(2-phenyl-imidazo[1,2-a]pyridin-7-yl)-amide]), 4.48 min (7-bromo-2-phenylimidazo[1,2-a]pyridine)). The yellow suspension was then cooled to room temperature and the solvent was evaporated under reduced pressure. The residue was crystallized from Me-THF. 2-Methyl-2H-pyrazole-3,4-dicarboxylic acid 4-dimethylamide 3-[(2-phenyl-imidazo[1,2-a]pyridin-7-yl)-amide] was obtained as a yellow crystalline solid (502 mg, 70% yield) with 99% purity (HPLC area-%).

HRMS: m/z=389.17 (M+H)+.

Example 5

5-[(2-(4-Fluoro-phenyl)-imidazo[1,2-a]pyridin-7-ylcarbamoyl]-1methyl-1H-pyrazole-4-carboxylic acid ethyl ester

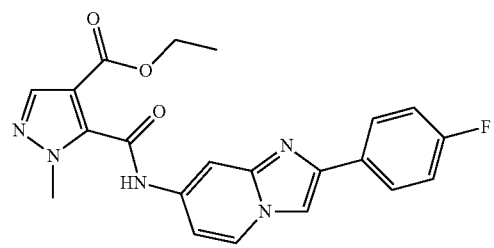 [SMILES: CCOC(=O)c1cnn(C)c1C(=O)Nc1ccn2cc(-c3ccc(F)cc3)nc2c1]

A suspension of tris(dibenzylideneacetone)dipalladium-chloroform adduct (7.6 mg, 7.4×10⁻³ mmol) and xantphos (8.7 mg, 14.8×10⁻³ mmol) in THF (2 mL) was added under argon to a 4-neck-round bottom flask containing ethyl 5-carbamoyl-1-methyl-1H-pyrazole-4-carboxylate (308 mg, 1.6 mmol), 7-bromo-2-(4-fluorophenyl)imidazo[1,2-a]pyridine (452 mg, 1.5 mmol), potassium carbonate (247 mg, 1.8 mmol) and EtOH (8 mL). The reaction mixture was heated at 80° C. for three hours. HPLC analysis of the reaction mixture showed >99% conversion (85% purity) (HPLC method cf. example 1.1. Retention times: 2.39 min (ethyl 5-carbamoyl-1-methyl-1H-pyrazole-4-carboxylate), 4.67 min (7-bromo-2-(4-fluorophenyl)imidazo[1,2-a]pyridine), 4.74 min (5-[(2-(4-fluoro-phenyl)-imidazo[1,2-a]pyridin-7-ylcarbamoyl]-1methyl-1H-pyrazole-4-carboxylic acid ethyl ester)). The yellow suspension was then cooled to room temperature and the solvent was evaporated under reduced pressure. The crude product was washed with an aqueous solution of potassium carbonate (2 mol/L) and then with water. After drying under vacuum, 5-[(2-(4-fluoro-phenyl)-imidazo[1,2-a]pyridin-7-ylcarbamoyl]-1methyl-1H-pyrazole-4-carboxylic acid ethyl ester was obtained as a yellow solid (548 mg, 91% yield) with 97% purity (HPLC area-%).

HRMS: m/z=408.15 (M+H)+.

Example 6

1-Methyl-5-(2-phenyl-imidazo[1,2,4]triazolo[1,5-a]pyridin-7-ylcarbamoyl)-1H-pyrazole-4-carboxylic acid ethyl ester

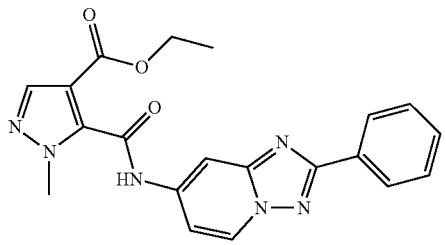

A suspension of tris(dibenzylideneacetone)dipalladium-chloroform adduct (9.0 mg, 8.7×10⁻³ mmol) and xantphos (10.4 mg, 17.6×10⁻³ mmol) in THF (2 mL) was added under argon to a pressure vessel containing ethyl 5-carbamoyl-1-methyl-1H-pyrazole-4-carboxylate (380 mg, 1.9 mmol), 7-bromo-2-phenyl-[1,2,4]triazolo[1,5-a]pyridine (500 mg, 1.8 mmol), potassium carbonate (290 mg, 2.1 mmol) and EtOH (8 mL). The reaction mixture was heated at 100° C. for three hours. The yellow suspension was then cooled to room temperature and the solvent was evaporated under reduced pressure. HPLC analysis of the residue showed >99% conversion (retention times: 2.39 min (ethyl 5-carbamoyl-1-methyl-1H-pyrazole-4-carboxylate, 4.62 min (7-bromo-2-phenyl-[1,2,4]triazolo[1,5-a]pyridine), 4.83 min (1-methyl-5-(2-phenyl-imidazo[1,2,4]triazolo[1,5-a]pyridin-7-ylcarbamoyl)-1H-pyrazole-4-carboxylic acid ethyl ester)). The crude product (99% purity by HPLC) was suspended in t-BuOH and filtered. The solid was washed with water and EtOH and then dried under vacuum. 1-Methyl-5-(2-phenyl-imidazo[1,2,4]triazolo[1,5-a]pyridin-7-ylcarbamoyl)-1H-pyrazole-4-carboxylic acid ethyl ester was obtained as a white solid (637 mg, 90% yield) with >99% purity (HPLC area-%).

HRMS: m/z=391.15 (M+H)+.

Example 7

4-(Azetidine-1-carbonyl)-2-methyl-2H-pyrazole-3-carboxylic acid (2-phenyl-[1,2,4]triazolo[1,5-a]pyridin-7-yl)-amide

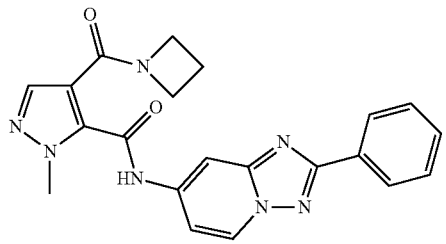 [SMILES: Cn1ncc(C(=O)N2CCC2)c1C(=O)Nc1ccn2nc(-c3ccccc3)nc2c1]

A suspension of tris(dibenzylideneacetone)dipalladium-chloroform adduct (9.5 mg, 9.1×10$^{-3}$ mmol) and xantphos (10.8 mg, 18.2×10$^{-3}$ mmol) in THF (2 mL) was added under argon to a 4-neck-round bottom flask containing 4-(azetidine-1-carbonyl)-1-methyl-1H-pyrazole-5-carboxamide (399 mg, 1.9 mmol), 7-bromo-2-phenyl-[1,2,4]triazolo[1,5-a]pyridine (500 mg, 1.8 mmol), potassium carbonate (306 mg, 2.2 mmol) and EtOH (8 mL). The reaction mixture was heated at 80° C. for one hour. HPLC analysis of the reaction mixture showed >99% conversion (96% purity) (HPLC method cf. example 1.1. Retention times: 1.51-1.70 min (4-(azetidine-1-carbonyl)-1-methyl-1H-pyrazole-5-carboxamide), 4.34 min (4-(azetidine-1-carbonyl)-2-methyl-2H-pyrazole-3-carboxylic acid (2-phenyl-[1,2,4]triazolo[1,5-a]pyridin-7-yl)-amide), 4.62 min (7-bromo-2-phenyl-[1,2,4]triazolo[1,5-a]pyridine)). The yellow suspension was then cooled to room temperature and the solvent was evaporated under reduced pressure. The residue was crystallized from Me-THF. 4-(Azetidine-1-carbonyl)-2-methyl-2H-pyrazole-3-carboxylic acid (2-phenyl-[1,2,4]triazolo[1,5-a]pyridin-7-yl)-amide was obtained as a yellow crystalline solid (570 mg, 78% yield) with >99% purity (HPLC area-%).

HRMS: m/z=402.17 (M+H)+.

Example 8

2-Methyl-2H-pyrazole-3,4-dicarboxylic acid 4-dimethylamide 3-[(2-phenyl-[1,2,4]triazolo[1,5-a]pyridin-7-yl)-amide]

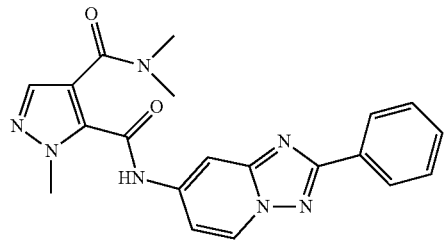 [SMILES: CN(C)C(=O)c1cnn(C)c1C(=O)Nc1ccn2nc(-c3ccccc3)nc2c1]

A suspension of tris(dibenzylideneacetone)dipalladium-chloroform adduct (9.4 mg, 9.1×10$^{-3}$ mmol) and xantphos (10.8 mg, 18.2×10$^{-3}$ mmol) in THF (2 mL) was added under argon to a 4-neck-round bottom flask containing 4-(Dimethylaminocarbonyl)-1-methyl-1H-pyrazole-5-carboxamide (376 mg, 1.9 mmol), 7-bromo-2-phenyl-[1,2,4]triazolo[1,5-a]pyridine (500 mg, 1.8 mmol), potassium carbonate (306 mg, 2.2 mmol) and EtOH (8 mL). The reaction mixture was heated at 80° C. for two hours. HPLC analysis of the reaction mixture showed >99% conversion (97% purity) (HPLC method cf. example 1.1. Retention times: 1.08 min (4-(Dimethylaminocarbonyl)-1-methyl-1H-pyrazole-5-carboxamide), 4.13 min (2-methyl-2H-pyrazole-3,4-dicarboxylic acid 4-dimethylamide 3-[(2-phenyl-[1,2,4]triazolo[1,5-a]pyridin-7-yl)-amide]), 4.62 min (7-bromo-2-phenyl-[1,2,4]triazolo[1,5-a]pyridine)). The yellow suspension was then cooled to room temperature and the solvent was evaporated under reduced pressure. The residue was crystallized from Me-THF. 2-Methyl-2H-pyrazole-3,4-dicarboxylic acid 4-dimethylamide 3-[(2-phenyl-[1,2,4]triazolo[1,5-a]pyridin-7-yl)-amide] was obtained as a yellow crystalline solid (382 mg, 54% yield) with >99% purity (HPLC area-%).

HRMS: m/z=390.17 (M+H)+.

Example 9

2-Methyl-2H-pyrazole-3,4-dicarboxylic acid 4-dimethylamide 3-[(2-morpholin-4-yl-[1,2,4]triazolo[1,5-a]pyridin-7-yl)-amide]

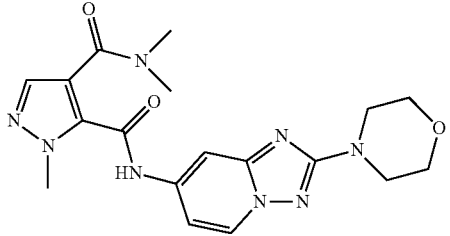 [SMILES: CN(C)C(=O)c1cnn(C)c1C(=O)Nc1ccn2nc(N3CCOCC3)nc2c1]

A suspension of tris(dibenzylideneacetone)dipalladium-chloroform adduct (1.8 mg, 1.7×10$^{-3}$ mmol) and xantphos (2.0 mg, 3.4×10$^{-3}$ mmol) in THF (0.4 mL) was added under argon to a 4-neck-round bottom flask containing 4-(Dimethylaminocarbonyl)-1-methyl-1H-pyrazole-5-carboxamide (72.3 mg, 368×10$^{-3}$ mmol), 4-(7-bromo-[1,2,4]triazolo[1,5- a]pyridine-2-yl)morpholine (96.3 mg, 340×10⁻³ mmol), potassium carbonate (57 mg, 408×10⁻³ mmol) and EtOH (1.6 mL). The reaction mixture was heated at 80° C. for two hours. HPLC analysis of the reaction mixture showed >99% conversion (87% purity) (HPLC method cf. example 1.1. Retention times: 1.08 min (4-(Dimethylaminocarbonyl)-1-methyl-1H-pyrazole-5-carboxamide), 3.03 min (2-methyl-2H-pyrazole-3,4-dicarboxylic acid 4-dimethylamide 3-[(2-morpholin-4-yl-[1,2,4]triazolo[1,5-a]pyridin-7-yl)-amide]), 3.25 min (4-(7-bromo-[1,2,4]triazolo[1,5-a]pyridin-2-yl)morpholine)). The yellow suspension was then cooled to room temperature and the solvent was evaporated under reduced pressure. The residue was dissolved in THF and filtered on a plug of silica. The solvent was evaporated under reduced pressure and the residue was suspended in t-BuOH. The product was collected by filtration. 2-Methyl-2H-pyrazole-3,4-dicarboxylic acid 4-dimethylamide 3-[(2-morpholin-4-yl-[1,2,4]triazolo[1,5-a]pyridin-7-yl)-amide] was obtained as a white solid (52 mg, 38% yield) with 96% purity (HPLC area-%).

HRMS: m/z=399.19 (M+H)+.

Example 10

1-Methyl-5-(2-morpholin-4-yl-[1,2,4]triazolo[1,5-a]pyridin-7-ylcarbamoyl)-1H-pyrazole-4-carboxylic acid ethyl ester

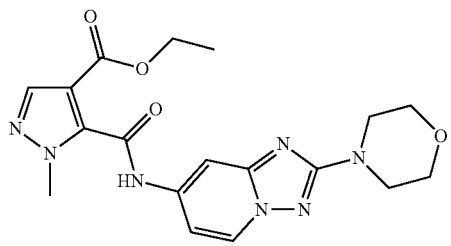 [SMILES: CCOC(=O)c1cnn(C)c1C(=O)Nc1ccn2nc(N3CCOCC3)nc2c1]

A suspension of tris(dibenzylideneacetone)dipalladium-chloroform adduct (9.1 mg, 8.8×10⁻³ mmol) and xantphos (10.4 mg, 17.7×10⁻³ mmol) in THF (2 mL) was added under argon to a 4-neck-round bottom flask containing ethyl 5-carbamoyl-1-methyl-1H-pyrazole-4-carboxylate (378 mg, 1.9 mmol), 4-(7-bromo-[1,2,4]triazolo[1,5-a]pyridine-2-yl)morpholine (500 mg, 1.8 mmol), potassium carbonate (296 mg, 2.1 mmol) and EtOH (8 mL). The reaction mixture was heated at 80° C. for four hours. HPLC analysis of the reaction mixture showed 99% conversion (73% purity) (HPLC method cf. example 1.1. Retention times: 2.39 min (ethyl 5-carbamoyl-1-methyl-1H-pyrazole-4-carboxylate), 3.25 min (4-(7-bromo-[1,2,4]triazolo[1,5-a]pyridin-2-yl)morpholine), 3.65 min (1-methyl-5-(2-morpholin-4-yl-[1,2,4]triazolo[1,5-a]pyridin-7-ylcarbamoyl)-1H-pyrazole-4-carboxylic acid ethyl ester)). The yellow suspension was then cooled to room temperature and the solvent was evaporated under reduced pressure. The residue was suspended in t-BuOH and filtered. The crude product was washed with water and dryed under vacuum. 1-Methyl-5-(2-morpholin-4-yl-[1,2,4]triazolo[1,5-a]pyridin-7-ylcarbamoyl)-1H-pyrazole-4-carboxylic acid ethyl ester was obtained as a light green solid (467 mg, 63% yield) with 94% purity (HPLC area-%).

HRMS: m/z=400.17 (M+H)+.

Example 11

4-(Azetidine-1-carbonyl)-2-methyl-2H-pyrazole-3-carboxylic acid (2-bromo-[1,2,4]triazolo[1,5-a]pyridin-7-yl)-amide

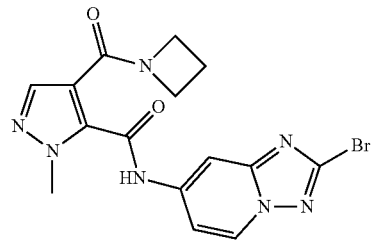 [SMILES: Cn1ncc(C(=O)N2CCC2)c1C(=O)Nc1ccn2nc(Br)nc2c1]

A suspension of tris(dibenzylideneacetone)dipalladium-chloroform adduct (9.3 mg, 9.0×10⁻³ mmol) and xantphos (10.7 mg, 18.1×10⁻³ mmol) in THF (2 mL) was added under argon to a 4-neck-round bottom flask containing 4-(azetidine-1-carbonyl)-1-methyl-1H-pyrazole-5-carboxamide (395 mg, 1.9 mmol), 2,7-dibromo-[1,2,4]triazolo[1,5-a]pyridine (500 mg, 1.8 mmol), potassium carbonate (302 mg, 2.2 mmol) and EtOH (8 mL). The reaction mixture was heated at 80° C. for one hour. HPLC analysis of the reaction mixture showed >99% conversion (HPLC method cf. example 1.1. Retention times: 1.51-1.70 min (4-(azetidine-1-carbonyl)-1-methyl-1H-pyrazole-5-carboxamide), 3.45 min (2,7-dibromo-[1,2,4]triazolo[1,5-a]pyridine), 3.68 min (4-(azetidine-1-carbonyl)-2-methyl-2H-pyrazole-3-carboxylic acid (2-bromo-[1,2,4]triazolo[1,5-a]pyridin-7-yl)-amide)). The yellow suspension was then cooled to room temperature and the solvent was evaporated under reduced pressure. The residue (85% HPLC purity) was suspended in Me-THF and filtered. The crude product was washed with water and dried under vacuum. 4-(Azetidine-1-carbonyl)-2-methyl-2H-pyrazole-3-carboxylic acid (2-bromo-[1,2,4]triazolo[1,5-a]pyridin-7-yl)-amide was obtained as a white solid (451 mg, 62% yield) with >99% purity (HPLC area-%).

HRMS: m/z=404.05 (M+H)+.

Example 12

7-{[4-(Azetidine-1-carbonyl)-2-methyl-2H-pyrazole-3-carbonyl]-amino}-[1,2,4]triazolo[1,5-a]pyridin-2-carboxylic acid ethyl ester

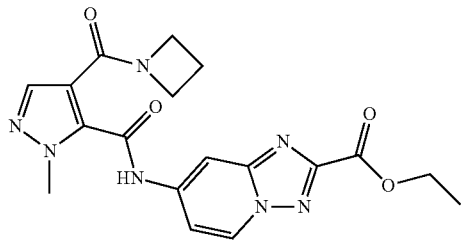 [SMILES: CCOC(=O)c1nc2cc(NC(=O)c3c(C(=O)N4CCC4)cnn3C)ccn2n1]

A suspension of tris(dibenzylideneacetone)dipalladium-chloroform adduct (9.6 mg, 9.3×10⁻³ mmol) and xantphos (10.9 mg, 18.5×10⁻³ mmol) in THF (2 mL) was added under argon to a 4-neck-round bottom flask containing 4-(azetidine-1-carbonyl)-1-methyl-1H-pyrazole-5-carboxamide (405 mg, 1.9 mmol), ethyl 7-bromo-[1,2,4]triazolo[1,5-a]pyridine-2-carboxylate (500 mg, 1.9 mmol), potassium carbonate (310 mg, 2.2 mmol) and EtOH (8 mL). The reaction mixture was heated at 80° C. for one hour. HPLC analysis of the reaction mixture showed >99% conversion (HPLC method cf. example 1.1. Retention times: 1.51-1.70 min (4-(azetidine-1-carbonyl)-1-methyl-1H-pyrazole-5-carboxamide), 3.16 min (ethyl 7-bromo-[1,2,4]triazolo[1,5-a]pyridine-2-carboxylate), 3.44 min (7-{[4-(azetidine-1-carbonyl)-2-methyl-2H-pyrazole-3-carbonyl]-amino}-[1,2,4]triazolo[1,5-a]pyridin-2-carboxylic acid ethyl ester)). The yellow suspension was then cooled to room temperature and the solvent was evaporated under reduced pressure. The residue (81% HPLC purity) was crystallized from Me-THF. 7-{[4-(Azetidine-1-carbonyl)-2-methyl-2H-pyrazole-3-carbonyl]-amino}-[1,2,4]triazolo[1,5-a]pyridin-2-carboxylic acid ethyl ester was obtained as a white solid (496 mg, 66% yield) with 97% purity (HPLC area-%). HRMS: m/z=398.16 (M+H)+.

Example 13

2-Methyl-4-(morpholine-4-carbonyl)-2H-pyrazole-3-carboxylic acid (2-phenyl-[1,2,4]triazolo[1,5-a]pyridin-7-yl)-amide

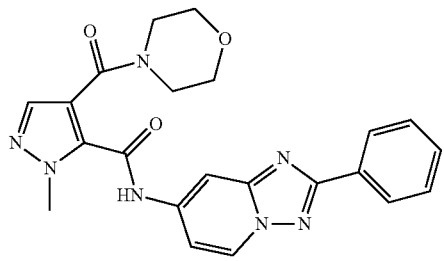 [SMILES: Cn1ncc(C(=O)N2CCOCC2)c1C(=O)Nc1ccn2nc(-c3ccccc3)nc2c1]

A suspension of tris(dibenzylideneacetone)dipalladium (32.0 mg, 35×10$^{-3}$ mmol) and xantphos (40.9 mg, 70.6×10$^{-3}$ mmol) in THF (8 mL) was added under argon to a 4-neck-round bottom flask containing 1-methyl-4-(4-morpholinylcarbonyl)-1H-pyrazole-5-carboxamide (1.84 g, 7.7 mmol), 7-bromo-2-phenyl-[1,2,4]triazolo[1,5-a]pyridine (2 g, 7.2 mmol), potassium carbonate (1.16 g, 8.3 mmol) and EtOH (32 mL). The reaction mixture was heated at 80° C. for three hours. HPLC analysis of the reaction mixture showed >99% conversion (71% purity) (HPLC method cf. example 1.1. Retention times: 1.11 min (1-methyl-4-(4-morpholinylcarbonyl)-1H-pyrazole-5-carboxamide), 4.08 min (2-methyl-4-(morpholine-4-carbonyl)-2H-pyrazole-3-carboxylic acid (2-phenyl-[1,2,4]triazolo[1,5-a]pyridin-7-yl)-amide), 4.62 min (7-bromo-2-phenyl-[1,2,4]triazolo[1,5-a]pyridine)). The volume of the reaction mixture was reduced to 28 mL. The suspension was filtered and the solid was washed with water and EtOH and then dried under vacuum. 2-Methyl-4-(morpholine-4-carbonyl)-2H-pyrazole-3-carboxylic acid (2-phenyl-[1,2,4]triazolo[1,5-a]pyridin-7-yl)-amide was obtained as a light gray solid (1.0 g, 32% yield) with 71% purity (HPLC area-%).
HRMS: m/z=431.17 (M+H)+.

We claim:
1. A process for the preparation of imidazo[1,2-a]pyridine compounds of the formula (I)

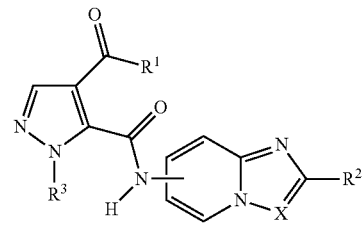

wherein $R^1$ is $C_{1-4}$-alkoxy or $NR^4R^5$ wherein $R^4$ and $R^5$ are independently hydrogen or $C_{1-4}$-alkyl, or, $R^4$ and $R^5$, together with the nitrogen atom to which they are attached, form a saturated 4- to 6-membered heterocyclic ring which may contain one additional heteroatom selected from nitrogen or oxygen;

$R^2$ is $C_{1-4}$-alkyl, $C_{1-4}$-alkoxycarbonyl, halogen, phenyl which is optionally substituted with $C_{1-4}$-alkyl, $C_{1-4}$-alkoxy or halogen or is $NR^4R^5$ wherein $R^4$ and $R^5$ are independently hydrogen or $C_{1-4}$-alkyl or $R^4$ and $R^5$, together with the nitrogen atom to which they are attached, form a saturated 4- to 6-membered heterocyclic ring which may contain one further heteroatom selected from nitrogen or oxygen;

$R^3$ is $C_{1-4}$-alkyl and

X is nitrogen or CH;

comprising the reaction of a pyrazole carboxamide derivative of formula (II)

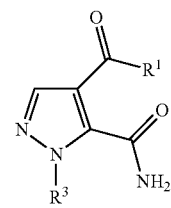

wherein $R^1$ and $R^3$ are as above;

with a halogen imidazo[1,2-a]pyridine derivative of the formula

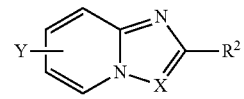

wherein $R^2$ and X are as above and Y is halogen, $C_{1-4}$-alkylsulfonyloxy, mono- or polyhalogen-$C_{1-4}$-alkylsulfonyloxy, mono- or poly-$C_{1-4}$-alkylphenylsulfonyloxy or phenylsulfonyloxy;

in the presence of a palladium catalyst, a base and an organic solvent.

2. The process of claim 1, wherein the palladium catalyst comprises a palladium source and a ligand of the formula (IV)

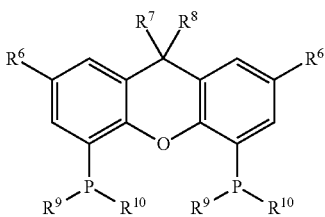

wherein $R^6$ is hydrogen or $C_{1-4}$-alkyl;

$R^7$ and $R^8$ are each independently $C_{1-4}$-alkyl;

$R^9$ and $R^{10}$ are each independently $C_{1-4}$-alkyl, $C_{3-7}$-cycloalkyl, di-($C_{1-4}$-alkyl)-amino or phenyl which is optionally substituted with $C_{1-4}$-alkyl or $C_{1-4}$-alkoxy, or $R^9$ and $R^{10}$ together form a cycle of the formula

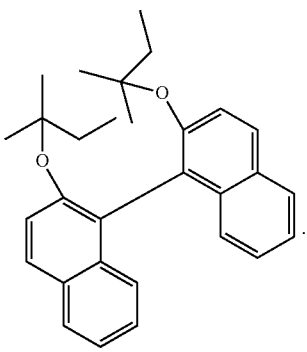 [SMILES: CCC(C)(C)Oc1ccc2ccccc2c1-c1c(OC(C)(C)CC)ccc2ccccc12]

3. The process of claim 2, wherein the palladium source can be is selected from Bis(dibenzylideneacetone)palladium (0), [Pd(dba)₂]; Tris(dibenzylideneacetone)dipalladium(0), [Pd₂(dba)₃]; Tris(dibenzylideneacetone)dipalladium(0)-chloroform adduct, [Pd₂(dba)₃].CHCl₃; Palladium(II) acetate, [Pd(OAc)₂]; Palladium(II) acetylacetonate, [Pd(acac)₂]; Bis(acetonitrile dichloropalladium(II)), [PdCl₂(CH₃CN)₂]; Palladium(II)Trifluoroacetate, [Pd(O₂CCF₃)₂]; di-μ-chlorobis[2-[(dimethylamino)methyl]phenyl-C,N]dipalladium(II), [Pd(C,N-Me₂NCH₂Ph)Cl₂]; or, Allylpalladium(II) chloride dimer, [Pd(allyl)Cl₂].

4. The process of claim 1 wherein the palladium catalyst comprises a palladium source selected from Tris(dibenzylideneacetone)dipalladium(0), [Pd₂(dba)₃] or from Tris (dibenzylideneacetone)dipalladium(0)-chloroform adduct, [Pd₂(dba)₃].CHCl₃ and a ligand of formula IV wherein $R^6$ is hydrogen;

$R^7$ and $R^8$ are methyl;

$R^9$ and $R^{10}$ are phenyl.

5. The process of claim 1 wherein the base is an organic base which can be selected from trialkylamines, amidines, alkali alcoholates and alkali acetates or is an inorganic base which can be selected from alkali- or alkali earth carbonates or -hydrogencarbonates, alkali- or alkali earth hydroxides, alkali- or alkali earth phosphates or -hydrogen phosphates.

6. The process of claim 5, wherein the base is potassium carbonate.

7. The process of claim 1 wherein the organic solvent is a polar protic solvent or a mixture of a polar protic solvent and a polar aprotic solvent.

8. The process of claim 7, wherein the organic solvent is ethanol or a mixture of ethanol and tetrahydrofuran.

9. The process of claim 1 wherein, the reaction is performed at a reaction temperature of 20° C. to 150° C.

10. The process of claim 1, wherein the imidazo[1,2-a]pyridine has the formula (Ib)

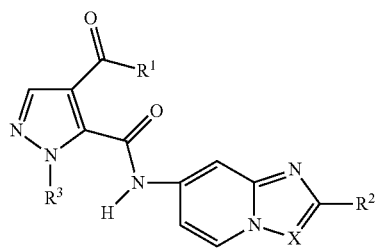

wherein $R^1$, $R^2$ and $R^3$ are as above and the halogen imidazo[1,2-a]pyridine derivative has the formula (Mb)

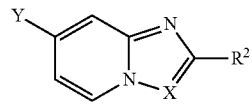

wherein $R^2$, X and Y are as above.

11. The process of claim 1, wherein $R^1$ is $C_{1-4}$-alkoxy or $NR^4R^5$ wherein $R^4$ and $R^5$ are independently $C_{1-4}$-alkyl or $R^4$ and $R^5$, together with the nitrogen atom to which they are attached, form a saturated 4- to 6-membered heterocyclic ring which may contain one further heteroatom selected from oxygen;

$R^2$ is $C_{1-4}$-alkoxycarbonyl, halogen, phenyl which is optionally substituted with halogen or is $NR^4R^5$ wherein $R^4$ and $R^5$, together with the nitrogen atom to which they are attached, form a saturated 4- to 6-membered heterocyclic ring which may contain one further heteroatom selected from oxygen;

$R^3$ is $C_{1-4}$-alkyl;

X is nitrogen or CH and

Y is chlorine, bromine, iodine, nonafluorbutanesulfonyloxy, mesityloxy or p-toluenesulfonyloxy.

\* \* \* \* \*